United States Patent [19]

Follenfant

[11] 4,012,517

[45] Mar. 15, 1977

[54] COMPOSITIONS AND TREATMENT

[75] Inventor: Michael John Follenfant, Croydon, England

[73] Assignee: Burroughs Wellcome Co., Raleigh, N.C.

[22] Filed: Jan. 23, 1976

[21] Appl. No.: 651,902

[30] Foreign Application Priority Data

Jan. 24, 1975 United Kingdom ............... 3141/75

[52] U.S. Cl. ............................... 424/269; 424/275; 424/276

[51] Int. Cl.² ................. A61K 31/38; A61K 31/39; A61K 31/41

[58] Field of Search ................... 424/269, 275, 276

[56] References Cited

UNITED STATES PATENTS 3,905,989    9/1975    Hodson et al. .................... 424/269

Primary Examiner—Stanley J. Friedman

[57] ABSTRACT

Substituted thioxanthone and phenoxathiin compounds having bronchodilating properties, and their use in the treatment or prophylaxis of bronchoconstriction in mammals.

9 Claims, No Drawings

COMPOSITIONS AND TREATMENT

This invention relates to the bronchodilator activity of certain tricyclic compounds.

Belgium Pat. No. 799,776 discloses compounds of formula (I)

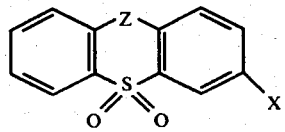

wherein Z is carbonyl (C=O) or oxygen (—O—) and X is 5 — tetrazolyl or carboxy, and salts thereof, as having antiallergic activity.

It has now been found that the compounds of formula (I) and their salts have bronchodilator properties in mammals, and in particular have a potent relaxant effect on isolated guinea pig tracheal strips.

Preferred compounds of formula (I) include 3-(5-tetrazolyl)thioxanthone 10,10-dioxide (formula (II)), 3-carboxythioxanthone 10,10-dioxide, and alkali metal salts thereof, especially sodium salts.

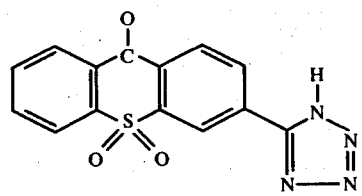

They may be made by conventional methods such as the methods described in the abovementioned Belgian patent.

The compounds of formula (I) and their pharmaceutically acceptable salts may be used to induce bronchodilation in mammals including man, and may thus be used in the treatment of prophylaxis of asthma including bronchial asthma, intermittent asthma and allergic asthma, bronchitis, pulmonary emphysema and other chronic respiratory diseases involving bronchospasm. Individual doses of from 0.1 to 15 mg/kg bodyweight may be used to treat mammals, the human dose being from about 3–15 mg/kg bodyweight per diem, preferably administered as an unit dose of from 50 to 400 mg. per adult human three times a day, more preferably from 100 – 250 mg. three times a day. These doses refer to the acid itself or are calculated as the acid where a salt thereof is used.

While the compounds of formula (I) or their salts may be administered to a mammal for inducing bronchodilation as the raw chemicals, they are conveniently presented for treatment or prophylaxis as an orally ingestible pharmaceutical composition comprising a compound of formula (I) or a salt thereof together with a pharmaceutically acceptable carrier. Advantageously the compositions take the form of discrete units, such as tablets, capsules or cachets each containing a predetermined amount of active ingredient. The compounds may also be presented as a powder or granules, to be administered either alone or in a solution or suspension in a liquid medium for oral administration.

The compositions may be made by any method known in the art of pharmacy, which include tabletting by compression or moulding, granulating, grinding, stirring, coating, milling and tumbling. One or more carriers may be included in a composition of this invention and these include diluents, solutes, buffers, flavouring, binding, dispersing, surface active, thickening, lubricating, and coating materials, preservatives, antioxidants and bacteriostats, and any other pharmaceutically acceptable excipients. Preferred pharmaceutical compositions contain from 5 to 95% by weight of active ingredient.

Included within the scope of the present invention as a feature which will be claimed is:

A method for inducing bronchodilation in a mammal comprising the administration to the mammal of a non-toxic, bronchodilation effective amount of a compound of formula (I) or a pharmaceutically acceptable salt thereof.

The following are Examples of this invention.

EXAMPLE 1

The compound of formula (II) provided a 50% relaxation of isolated guinea pig tracheal strips at a concentration of 2.0μM.

EXAMPLE 2

3-Carboxythioxanthone 10,10-dioxide provided a 50% relaxation of isolated guinea pig tracheal strips at a concentration of 1.3μM.

EXAMPLE 3

2-(5-Tetrazolyl)phenoxathiin 10,10-dioxide provided a 50% relaxation of isolated guinea pig tracheal strips at a concentration of 2.0μM.

What I claim is:

1. A method for treating bronchoconstriction in a mammal by dilating the bronchi of the mammal comprising administration to a mammal having a bronchoconstriction of a non-toxic effective bronchodilating amount of a compound of formula (I)

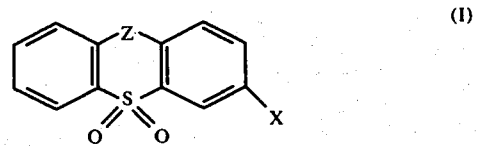

where Z is carbonyl or oxygen and X is 5-tetrazolyl or carboxyl, and pharmaceutically acceptable salts thereof.

2. A method as claimed in claim 1 wherein the compound of formula (I) is selected from:
   2-(5-tetrazolyl)phenoxathiin-10,10-dioxide;
   3-(5-tetrazolyl)thioxanthone-10,10-dioxide;
   3-carboxylthioxanthone-10,10-dioxide;
   and pharmaceutically acceptable salts thereof.

3. A method as claimed in claim 1 wherein the compound of formula (I) is 3-(5-tetrazolyl)thioxanthone-10,10-dioxide.

4. A method as claimed in claim 1 for the treatment or prophylaxis of asthma, bronchitis or pulmonary emphysema.

5. A method as claimed in claim 1 comprising the administration of a compound of formula (I) in a dose of from 0.1 to 15 mg per kg bodyweight of the mammal to be treated.

6. A method as claimed in claim 5 wherein the dose is from 3 to 15 mg per kg bodyweight.

7. A method as claimed in claim 5 wherein the dose is from 1 to 5 mg per kg bodyweight.

8. A method as claimed in claim 1 wherein the compound of formula (I) is administered at a dose of from 50 to 400 mg.

9. A method as claimed in claim 7 wherein the dose is from 100 to 250 mg.

* * * * *